(12) United States Patent
Ito et al.

(10) Patent No.: US 10,280,120 B2
(45) Date of Patent: *May 7, 2019

(54) ZIRCONIA COMPOSITION, ZIRCONIA PRE-SINTERED BODY AND ZIRCONIA SINTERED BODY, AND DENTAL PRODUCT

(71) Applicant: KURARAY NORITAKE DENTAL INC., Kurashiki-shi (JP)

(72) Inventors: Yoshihisa Ito, Miyoshi (JP); Atsushi Matsumoto, Miyoshi (JP); Tomohiro Emoto, Miyoshi (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/596,750

(22) Filed: May 16, 2017

(65) Prior Publication Data

US 2017/0247295 A1  Aug. 31, 2017

Related U.S. Application Data

(63) Continuation of application No. 15/522,965, filed as application No. PCT/JP2015/080728 on Oct. 30, 2015.

(30) Foreign Application Priority Data

Oct. 31, 2014 (JP) ................. 2014-223636

(51) Int. Cl.
| | |
|---|---|
| C04B 35/48 | (2006.01) |
| C04B 35/486 | (2006.01) |
| A61C 13/083 | (2006.01) |
| A61K 6/02 | (2006.01) |
| A61C 5/73 | (2017.01) |
| C04B 35/64 | (2006.01) |
| C04B 41/00 | (2006.01) |
| C04B 41/50 | (2006.01) |
| C04B 41/87 | (2006.01) |
| C09C 1/00 | (2006.01) |
| A61C 13/00 | (2006.01) |
| A61K 6/00 | (2006.01) |
| C04B 35/488 | (2006.01) |
| C04B 35/626 | (2006.01) |

(Continued)

(52) U.S. Cl.
CPC ............ *C04B 35/48* (2013.01); *A61C 5/73* (2017.02); *A61C 13/0022* (2013.01); *A61C 13/083* (2013.01); *A61K 6/0094* (2013.01); *A61K 6/024* (2013.01); *A61K 6/025* (2013.01); *C04B 35/486* (2013.01); *C04B 35/488* (2013.01); *C04B 35/6261* (2013.01); *C04B 35/62625* (2013.01); *C04B 35/62675* (2013.01); *C04B 35/62695* (2013.01); *C04B 35/64* (2013.01); *C04B 35/6455* (2013.01); *C04B 41/009* (2013.01); *C04B 41/5038* (2013.01); *C04B 41/87* (2013.01); *C09C 1/0009* (2013.01); *C09C 1/0012* (2013.01); *C04B 2111/00836* (2013.01); *C04B 2111/82* (2013.01); *C04B 2235/3206* (2013.01); *C04B 2235/3208* (2013.01); *C04B 2235/3217* (2013.01); *C04B 2235/3224* (2013.01); *C04B 2235/3225* (2013.01); *C04B 2235/3229* (2013.01); *C04B 2235/3232* (2013.01); *C04B 2235/3239* (2013.01); *C04B 2235/3241* (2013.01); *C04B 2235/3243* (2013.01); *C04B 2235/3244* (2013.01); *C04B 2235/3248* (2013.01); *C04B 2235/3251* (2013.01); *C04B 2235/3262* (2013.01); *C04B 2235/3272* (2013.01); *C04B 2235/3274* (2013.01); *C04B 2235/3275* (2013.01); *C04B 2235/3279* (2013.01); *C04B 2235/3418* (2013.01); *C04B 2235/3427* (2013.01); *C04B 2235/602* (2013.01); *C04B 2235/604* (2013.01); *C04B 2235/6026* (2013.01); *C04B 2235/656* (2013.01); *C04B 2235/668* (2013.01); *C04B 2235/762* (2013.01); *C04B 2235/765* (2013.01); *C04B 2235/9661* (2013.01)

(58) Field of Classification Search
CPC ...... C04B 35/48; C04B 35/486; A61C 13/081
See application file for complete search history.

(56) References Cited

U.S. PATENT DOCUMENTS

| | | | | |
|---|---|---|---|---|
| 4,170,823 A | * | 10/1979 | Smyth | .................. A61K 6/0005 250/461.1 |
| 5,263,858 A | * | 11/1993 | Yoshida | ................... A61C 7/00 433/8 |

(Continued)

FOREIGN PATENT DOCUMENTS

| | | |
|---|---|---|
| EP | 2 995 434 A1 | 3/2016 |
| EP | 3 159 323 A1 | 4/2017 |

(Continued)

OTHER PUBLICATIONS

Extended European Search Report dated Dec. 11, 2017 in Patent Application No. 17180987.4, 8 pages.

(Continued)

*Primary Examiner* — Karl E Group
(74) *Attorney, Agent, or Firm* — Oblon, McClelland, Maier & Neustadt, L.L.P.

(57) ABSTRACT

Provided is a zirconia sintered body that suppresses discoloration due to porcelain. The zirconia sintered body comprises at least one of a coloring agent A: erbium oxide and a coloring agent B: nickel oxide, and a composite oxide of zirconium and vanadium.

27 Claims, No Drawings

(51) Int. Cl.
  *C04B 35/645* (2006.01)
  *C04B 111/00* (2006.01)
  *C04B 111/82* (2006.01)

(56) References Cited

U.S. PATENT DOCUMENTS

| | | | |
|---|---|---|---|
| 5,466,285 A * | 11/1995 | Kamiya | C04B 33/24 |
| | | | 106/35 |
| 7,494,539 B2 * | 2/2009 | Ikushima | C04B 35/486 |
| | | | 106/35 |
| 7,497,963 B2 | 3/2009 | Khan et al. | |
| 7,497,983 B2 * | 3/2009 | Khan | A61C 13/0003 |
| | | | 264/17 |
| 9,126,870 B2 | 9/2015 | Nahas et al. | |
| 9,212,065 B2 * | 12/2015 | Yamada | C01G 25/02 |
| 9,428,422 B2 * | 8/2016 | Kawamura | A61K 6/0005 |
| 2007/0182042 A1 | 8/2007 | Ikushima et al. | |
| 2008/0085828 A1 | 4/2008 | Khan et al. | |
| 2012/0121859 A1 | 5/2012 | Nahas et al. | |
| 2014/0328746 A1 * | 11/2014 | Yamada | C01G 25/02 |
| | | | 423/608 |
| 2015/0223917 A1 | 8/2015 | Herrmann et al. | |
| 2015/0315086 A1 * | 11/2015 | Kawamura | A61K 6/0005 |
| | | | 501/134 |
| 2016/0074142 A1 | 3/2016 | Yamada et al. | |
| 2017/0143458 A1 | 5/2017 | Fujisaki et al. | |

FOREIGN PATENT DOCUMENTS

| | | |
|---|---|---|
| FR | 2 947 261 A1 | 12/2010 |
| JP | 62-59571 A | 3/1987 |
| JP | 3-242345 A | 10/1991 |
| JP | 2007-126360 A | 5/2007 |
| JP | 2007-190215 A | 8/2007 |
| JP | 2007-210822 A | 8/2007 |
| JP | 2011-20878 A | 2/2011 |
| JP | 2016-88793 A | 5/2016 |
| WO | WO 2008/021495 A2 | 2/2008 |
| WO | WO 2014/046949 A1 | 3/2014 |

OTHER PUBLICATIONS

International Search Report dated Feb. 2, 2016 in PCT/JP2015/080728 filed Oct. 30, 2015.

\* cited by examiner

ZIRCONIA COMPOSITION, ZIRCONIA PRE-SINTERED BODY AND ZIRCONIA SINTERED BODY, AND DENTAL PRODUCT

REFERENCE TO RELATED APPLICATION

This application is a continuation of U.S. application Ser. No. 15/522,965, filed on Apr. 28, 2017, which claims the benefit of the priority of Japanese patent application No. 2014-223636 filed on Oct. 31, 2014, the disclosure of which is incorporated herein in its entirety by reference thereto.

TECHNICAL FIELD

The present invention relates to a zirconia sintered body containing a pigment. The present invention also relates to a zirconia composition and a zirconia pre-sintered body for producing the zirconia sintered body. The present invention further relates to a dental product using the zirconia sintered body.

BACKGROUND

In recent years, ceramic such as zirconia etc. has been used as a dental prosthesis (a covering crown, a tooth crown, a crown, a false (artificial) tooth etc.) instead of metal in view of aesthetics and safety. Further, it has been conducted to reproduce the appearance of a natural tooth by baking porcelain such as glass on a ceramic frame (refer to, for example, Patent Literature 1).

CITATION LIST

Patent Literatures (PTL)

PTL 1: JP Patent Kokai Publication No. JP2007-126360A

SUMMARY

The following analyses are given in view of the present invention.

In order to make a prosthesis look like a natural tooth, there is a case where a coloring ingredient is added also to ceramic per se as a base material. Because a natural tooth is usually tinged with a yellowish and reddish tone, a coloring agent which develops yellow and red is added to the ceramic. In many cases, a praseodymium compound and an iron compound which are safe for human body are added as these yellow based- and red based-coloring agents. However, there were cases where desired color development may not be obtained by building up and baking porcelain on a ceramic to which a praseodymium compound and/or an iron compound is added. This is thought to be because an antimony compound, a cerium compound etc. which are added to porcelain as an anti-yellowing (yellowing prevention) material suppress color development by the praseodymium compound, an iron compound etc. Accordingly, such ceramic is desired that is able to reproduce the same color as a natural tooth without its color development being suppressed by an antimony compound, a cerium compound etc.

According to a first aspect of the present invention, a zirconia sintered body is provided, the zirconia sintered body comprising at least one of a coloring agent A: erbium oxide and a coloring agent B: nickel oxide; and a coloring agent C: a composite oxide of zirconium and vanadium.

According to a second aspect of the present invention, a zirconia sintered body is provided, the zirconia sintered body comprising at least one coloring agent selected from the group including (consisting of) a coloring agent A: erbium oxide, a coloring agent B: nickel oxide, a coloring agent C: a composite oxide of zirconium and vanadium, a coloring agent D: a mixture of a composite oxide of iron, cobalt and chromium, a composite oxide of zirconium and silicon, silicon dioxide and nickel oxide, and a coloring agent E: a composite oxide of zirconium, silicon, cobalt and nickel.

According to a third aspect of the present invention, a composition comprising zirconium oxide, yttrium oxide, and a coloring agent is provided. The coloring agent comprises at least one of a coloring agent A: erbium oxide and a coloring agent B: nickel oxide; and a coloring agent C: a composite oxide of zirconium and vanadium.

According to a fourth aspect of the present invention, a composition comprising zirconium oxide, yttrium oxide, and a coloring agent is provided. The coloring agent comprises at least one coloring agent selected from the group including a coloring agent A: erbium oxide, a coloring agent B: nickel oxide, a coloring agent C: a composite oxide of zirconium and vanadium, a coloring agent D: a mixture of a composite oxide of iron, cobalt and chromium, a composite oxide of zirconium and silicon, silicon dioxide and nickel oxide, and a coloring agent E: a composite oxide of zirconium, silicon, cobalt and nickel.

According to a fifth aspect of the present invention, a pre-sintered body comprising zirconium oxide, yttrium oxide, and a coloring agent is provided. The coloring agent comprises at least one of a coloring agent A: erbium oxide and a coloring agent B: nickel oxide; and a coloring agent C: a composite oxide of zirconium and vanadium.

According to a sixth aspect of the present invention, a pre-sintered body comprising zirconium oxide, yttrium oxide, and a coloring agent is provided. The coloring agent comprises at least one coloring agent selected from the group including a coloring agent A: erbium oxide, a coloring agent B: nickel oxide, a coloring agent C: a composite oxide of zirconium and vanadium, a coloring agent D: a mixture of a composite oxide of iron, cobalt and chromium, a composite oxide of zirconium and silicon, silicon dioxide and nickel oxide, and a coloring agent E: a composite oxide of zirconium, silicon, cobalt and nickel.

According to a seventh aspect of the present invention, a dental product is provided, the dental product comprising a zirconia sintered body according to any one of the above aspects.

It can be achieved to suppress discoloration of a zirconia sintered body even if porcelain which contains an antimony compound and/or a cerium compound is baked.

PREFERRED EMBODIMENTS

Preferred modes for the above aspects will be described below.

According to a preferred mode for the first aspect, the zirconia sintered body comprises a coloring agent A of 0.002 mass % to 0.4 mass %, a coloring agent B of 0.0002 mass % to 0.03 mass %, and a coloring agent C of 0.005 mass % to 0.1 mass %.

According to a preferred mode for the first aspect, the zirconia sintered body comprises a coloring agent B of 0.01 mass % to 0.02 mass %, and a coloring agent C of 0.06 mass % to 0.08 mass %.

According to a preferred mode for the second aspect, the zirconia sintered body comprises at least one of a coloring agent A, a coloring agent B and a coloring agent C, and at least one of a coloring agent D and a coloring agent E.

According to a preferred mode for the second aspect, the zirconia sintered body comprises a coloring agent C of 0.005 mass % to 0.02 mass %, and a coloring agent E of 0.06 mass % to 0.08 mass %.

According to a preferred mode for the second aspect, the zirconia sintered body comprises a coloring agent C of 0.07 mass % to 0.09 mass %, and a coloring agent D of 0.05 mass % to 0.2 mass %.

According to a preferred mode for the second aspect, the zirconia sintered body comprises a coloring agent B of 0.007 mass % to 0.06 mass %, and a coloring agent D of 0.01 mass % to 0.06 mass %.

According to a preferred mode for the second aspect, the zirconia sintered body comprises a coloring agent A of 0.01 mass % to 0.04 mass %, a coloring agent C of 0.05 mass % to 0.07 mass %, and a coloring agent D of 0.05 mass % to 0.08 mass %.

According to a preferred mode for the second aspect, the zirconia sintered body comprises a coloring agent A of 0.002 mass % to 0.3 mass %, a coloring agent B of 0.0005 mass % to 0.03 mass %, a coloring agent C of 0.005 mass % to 0.07 mass %, and a coloring agent D of 0.004 mass % to 0.04 mass %.

According to a preferred mode for the third aspect, the composition comprises a coloring agent A of 0.002 mass % to 0.4 mass %, a coloring agent B of 0.0002 mass % to 0.03 mass %, and a coloring agent C of 0.005 mass % to 0.1 mass %.

According to a preferred mode for the third aspect, the composition comprises a coloring agent B of 0.01 mass % to 0.02 mass %, and a coloring agent C of 0.06 mass % to 0.08 mass %.

According to a preferred mode for the fourth aspect, the composition comprises at least one of a coloring agent A, a coloring agent B and a coloring agent C, and at least one of a coloring agent D and a coloring agent E.

According to a preferred mode for the fourth aspect, the composition comprises a coloring agent C of 0.02 mass % to 0.03 mass %, and a coloring agent E of 0.06 mass % to 0.08 mass %.

According to a preferred mode for the fourth aspect, the composition comprises a coloring agent C of 0.07 mass % to 0.09 mass %, and a coloring agent D of 0.08 mass % to 0.12 mass %.

According to a preferred mode for the fourth aspect, the composition comprises a coloring agent B of 0.007 mass % to 0.06 mass %, and a coloring agent D of 0.01 mass % to 0.06 mass %.

According to a preferred mode for the fourth aspect, the composition comprises a coloring agent A of 0.01 mass % to 0.04 mass %, a coloring agent C of 0.05 mass % to 0.07 mass %, and a coloring agent D of 0.05 mass % to 0.08 mass %.

According to a preferred mode for the fourth aspect, the composition comprises a coloring agent A of 0.002 mass % to 0.3 mass %, a coloring agent B of 0.0005 mass % to 0.03 mass %, a coloring agent C of 0.005 mass % to 0.07 mass %, and a coloring agent D of 0.004 mass % to 0.04 mass %.

According to a preferred mode for the fourth aspect, a pre-sintered body is provided, the pre-sintered body being produced by firing the composition at 800° C. to 1200° C.

According to a preferred mode for the fourth aspect, a zirconia sintered body is provided, the zirconia sintered body being produced by firing the composition at 1300° C. to 1600° C.

According to a preferred mode for the fifth aspect, the pre-sintered body comprises a coloring agent A of 0.002 mass % to 0.4 mass %, a coloring agent B of 0.0002 mass % to 0.03 mass %, and a coloring agent C of 0.005 mass % to 0.1 mass %.

According to a preferred mode for the fifth aspect, the pre-sintered body comprises a coloring agent B of 0.01 mass % to 0.02 mass %, and a coloring agent C of 0.06 mass % to 0.08 mass %.

According to a preferred mode for the sixth aspect, the pre-sintered body comprises at least one of a coloring agent A, a coloring agent B and a coloring agent C, and at least one of a coloring agent D and a coloring agent E.

According to a preferred mode for the sixth aspect, the pre-sintered body comprises a coloring agent C of 0.02 mass % to 0.03 mass %, and a coloring agent E of 0.06 mass % to 0.08 mass %.

According to a preferred mode for the sixth aspect, the pre-sintered body comprises a coloring agent C of 0.07 mass % to 0.09 mass %, and a coloring agent D of 0.08 mass % to 0.12 mass %.

According to a preferred mode for the sixth aspect, the pre-sintered body comprises a coloring agent B of 0.007 mass % to 0.06 mass %, and a coloring agent D of 0.01 mass % to 0.06 mass %.

According to a preferred mode for the sixth aspect, the pre-sintered body comprises a coloring agent A of 0.01 mass % to 0.04 mass %, a coloring agent C of 0.05 mass % to 0.07 mass %, and a coloring agent D of 0.05 mass % to 0.08 mass %.

According to a preferred mode for the sixth aspect, the pre-sintered body comprises a coloring agent A of 0.002 mass % to 0.3 mass %, a coloring agent B of 0.0005 mass % to 0.03 mass %, a coloring agent C of 0.005 mass % to 0.07 mass %, and a coloring agent D of 0.004 mass % to 0.04 mass %.

According to a preferred mode for the sixth aspect, a zirconia sintered body is provided, the zirconia sintered body being produced by firing (sintering) the pre-sintered body at 1300° C. to 1600° C.

According to a preferred mode for the seventh aspect, the dental product further comprises a porcelain layer laminated on the zirconia sintered body. The porcelain layer comprises a yellowing prevention material.

According to a preferred mode for the seventh aspect, the yellowing prevention material comprises at least one of an antimony compound and a cerium compound.

A zirconia sintered body of a first mode according to the present invention will be described below. A zirconia sintered body of the present invention is a sintered body in which partially-stabilized zirconia crystal particles are mainly (as a main component) sintered, and has the partially-stabilized zirconia as a matrix phase. In the zirconia sintered body of the present invention, a main crystal phase of zirconia is at least one of a tetragonal crystal system and a cubic crystal system. Zirconia may have both a tetragonal crystal system and a cubic crystal system. Preferably, the zirconia sintered body has substantially no monoclinic crystal system in a stage of not undergoing a hydrothermal treatment test.

A zirconia sintered body of the present invention includes not only a sintered body made by sintering shaped (compacted or molded) zirconia particles under normal pressure or under application of no pressure, but also a sintered body densified by high temperature pressurization treatment such as HIP (Hot Isostatic Pressing) treatment etc.

A zirconia sintered body of the present invention comprises zirconium oxide (zirconia), a stabilizer therefor, and a coloring agent. The zirconia sintered body may comprise an additional additive or additives. The additive includes, for example, titanium oxide, aluminum oxide, silicon dioxide etc.

A stabilizer for a partially-stabilized zirconia includes, for example, [an oxide of] an oxide or oxides such as calcium oxide (CaO), magnesium oxide (MgO), yttrium oxide ($Y_2O_3$) (hereinafter referred to as "yttria"), cerium oxide ($CeO_2$) etc. In a case of using a coloring agent described hereinafter, yttria is used more preferably. Preferably, the stabilizer is added in an amount sufficient to partially stabilize zirconia. For example, in a case of using yttrium oxide as a stabilizer, yttrium oxide to be added may be contained in the whole zirconia sintered body preferably in a concentration of 2 mol % to 7 mol % for the partially stabilized zirconium oxide. The content (ratio) of a stabilizer in a zirconia sintered body may be measured for example by Inductively Coupled Plasma (ICP) emission spectral analysis, fluorescence X-ray analysis etc. Incidentally, zirconia partially stabilized by addition of a stabilizer is called Partially Stabilized Zirconia (PSZ).

Next, the following will explain a composition and a pre-sintered body for production of a zirconia sintered body according to the present invention. A composition and a pre-sintered body are a precursor (an intermediate or semi-finished product) of the above-mentioned zirconia sintered body according to the present invention. A pre-sintered body is obtained by firing (i.e. calcining) a composition at such a temperature that it does not reach "sintering" (or a sintered state) (i.e. by pre-sintering the composition). A pre-sintered body also includes one that has been processed (or machined) for shaping. For example, a pre-sintered body also encompasses a dental product (such as a crown-shaped prosthesis) obtained by working a pre-sintered zirconia disc using a CAD/CAM (Computer-Aided Design/Computer-Aided manufacturing) system.

A composition and a pre-sintered body contain a zirconia crystal particle(s), a stabilizer and a coloring agent (pigment). The composition and the pre-sintered body may contain other additives. The additive includes, for example, titanium oxide, aluminum oxide, silicon dioxide etc.

A stabilizer in a composition and a pre-sintered body includes, for example, an oxide such as calcium oxide (CaO), magnesium oxide (MgO), yttria, cerium oxide ($CeO_2$) etc. A stabilizer is preferably added in an amount enough to partially stabilize tetragonal zirconia particles. For example, if yttria is used as a stabilizer, the content of yttria may be preferably 2 mol % to 7 mol % relative to the total mole of zirconia and yttria.

The composition according to the present invention also encompasses powder, fluid obtained by adding powder to solvent, and a shaped body obtained by shaping powder(s) in a predetermined shape. That is, the composition may be a powdered one, or a paste-like or wet one (i.e. the composition may be contained in a solvent or may contain a solvent). Further, the composition may be one containing an additive such as a binder, a pigment etc. Incidentally, in calculation of the above-mentioned content, the mass of an additive such as solvent, a binder etc. is not considered.

A composition according to the present invention, if it is a shaped body, may be shaped by any shaping (forming) method, for example by a press molding method, an injection molding method or an optical forming method, or may be shaped in a multi-stage manner. For example, a composition according to the present invention may be press-formed followed by subjecting to CIP (Cold Isostatic Pressing).

A pre-sintered body according to the present invention can be obtained by firing a composition according to the present invention under normal pressure at 800° C. to 1200° C.

A pre-sintered body according to the present invention is fired under normal pressure at 1350° C. to 1600° C., resulting in a zirconia sintered body according to the present invention.

A sintered body, a composition and a pre-sintered body according to the present invention may contain, as a coloring ingredient, at least one of a metal oxide and a commercially available coloring agent. A zirconia sintered body, a composition and a pre-sintered body having chromaticity as mentioned above may contain at least one oxide or compound selected from the group including, for example, erbium oxide ($Er_2O_3$); nickel oxide (NiO); a composite oxide of zirconium and vanadium (($Zr, V)O_2$); a composite oxide of iron, cobalt and chromium (($Co, Fe)(Fe, Cr)_2O_4$); a composite oxide of zirconium and silicon (zircon ($ZrSiO_4$)); silicon dioxide ($SiO_2$); and a composite oxide of zirconium, silicon, cobalt and nickel (($Co, Ni)O \cdot ZrSiO_4$).

In the following, the content of a coloring agent means a ratio of its mass to a total mass of zirconia, a stabilizer(s) and a coloring agent(s) contained in a zirconia sintered body, a composition and a pre-sintered body. Further, in a zirconia sintered body and a pre-sintered body, a coloring agent does not necessarily exist in a form of a compound before firing. A coloring agent may have reacted with an ingredient(s) in a zirconia sintered body and a pre-sintered body. In the present application, the content of a coloring agent in a zirconia sintered body, a composition and a pre-sintered body is calculated on the basis of a compound before firing (at the time of addition). The chemical formulas set forth in the Description and the Claims show representative constitutions for better understanding of their constitutional contents and thus do not necessarily strictly show their stoichiometric constitutional relations. Allowable ranges of the above-mentioned constitutions are naturally determined according to practically available materials in order to carry out the present invention and achieve its effect.

A zirconia sintered body, a composition and a pre-sintered body may contain, for example, erbium oxide ($Er_2O_3$) (hereinafter referred to as "coloring agent A"). A zirconia sintered body, a composition and a pre-sintered body may contain nickel oxide (NiO) (hereinafter referred to as "coloring agent B"). A zirconia sintered body, a composition and a pre-sintered body may contain a composite oxide of zirconium and vanadium (($Zr, V)O_2$) (hereinafter referred to as "coloring agent C"). A zirconia sintered body, a composition and a pre-sintered body may contain a mixture containing a composite oxide of iron, cobalt and chromium (($Co, Fe)(Fe, Cr)_2O_4$); a composite oxide of zirconium and silicon (zircon ($ZrSiO_4$)); silicon dioxide ($SiO_2$); and nickel oxide (NiO) (($Co, Fe)(Fe, Cr)_2O_4/ZrSiO_4/SiO_2/NiO$) (hereinafter referred to as "coloring agent D"). A zirconia sintered body, a composition and a pre-sintered body may also contain a composite oxide of zirconium, silicon, cobalt and nickel (($Co, Ni)O \cdot ZrSiO_4$) (hereinafter referred to as "coloring agent E"). A zirconia sintered body, a composition and a pre-sintered body may contain at least one coloring agent selected from the group including the coloring agent A, the coloring agent B, the coloring agent C, the coloring agent D and the coloring agent E.

By addition of the coloring agent A, a zirconia sintered body tends to take on a red tinge. By addition of the coloring agent B, a zirconia sintered body tends to take on a red tinge. By addition of the coloring agent C, a zirconia sintered body tends to take on a yellow tinge. By addition of the coloring agent D, a zirconia sintered body tends to take on a gray tinge. By addition of the coloring agent E, a zirconia sintered body tends to take on a gray tinge. In particular, a composite oxide of zirconium and vanadium ((Zr, V)O$_2$) (e.g. the coloring agent C), for example, may be used instead of praseodymium oxide (Pr$_6$O$_{11}$). Instead of iron oxide (Fe$_2$O$_3$), erbium oxide (Er$_2$O$_3$) (e.g. the coloring agent A) and/or nickel oxide (NiO) (e.g. the coloring agent B) may be used.

Each coloring agent may also contain other ingredient(s) than the ingredients as enumerated above. For example, the coloring agent C may contain an iron compound, a nickel compound, a niobium compound, a titanium compound etc. as an ingredient other than the above ingredients. For example, the coloring agent D may contain a manganese compound, a vanadium compound etc. as an ingredient other than the above ingredients. For example, the coloring agent E may contain an iron compound as an ingredient other than the above ingredients. Each coloring agent may also contain an ingredient which is not involved in color development, as an ingredient other than the ingredient involved in color development of a zirconia sintered body.

In the following, as to the content of the coloring agent B, a NiO ingredient contained in the other coloring agents than the coloring agent B is not considered. In any one of the combinations of the above coloring agents, the content of each coloring agent can be adjusted, for example, such that a total amount of a NiO ingredient does not exceed a given upper limit or does not fall below a given lower limit.

A zirconia sintered body, a composition and a pre-sintered body may contain at least two coloring agents of the coloring agent A, the coloring agent B, the coloring agent C, the coloring agent D and the coloring agent E. A zirconia sintered body, a composition and a pre-sintered body may contain the coloring agent A of 0 mass % to 0.5 mass %. A zirconia sintered body, a composition and a pre-sintered body may contain the coloring agent B of 0 mass % to 0.06 mass %. A zirconia sintered body, a composition and a pre-sintered body may contain the coloring agent C of 0 mass % to 0.2 mass %. A zirconia sintered body, a composition and a pre-sintered body may contain the coloring agent D of 0 mass % to 0.2 mass %. A zirconia sintered body, a composition and a pre-sintered body may contain the coloring agent E of 0 mass % to 0.1 mass %.

As the coloring agent C, "Z-300 YELLOW" made by NITTO GANRYO KOGYO CO., LTD., for example, may be used. As the coloring agent D, "4555 GRAY" made by KAWAMURA-CHEMICAL CO., LTD., for example, may be used. As the coloring agent E, "H-150 GRAY" made by NITTO GANRYO KOGYO CO., LTD., for example, may be used.

Preferably, the zirconia sintered body according to the first embodiment has L* of 64 to 76, a* of −6 to 3 and b* of 3 to 27 in the L*a*b* color system (Lab color space). The zirconia sintered body having such chromaticity can show a natural tooth-like color.

In the present disclosure, chromaticities (L*, a*, b*) in the L*a*b* color system are numerical values obtained by measuring a sample produced as the below-described examples in a black background.

Next, the following will explain an example of a method of producing a composition, a pre-sintered body and a zirconia sintered body according to the present invention.

Initially, zirconia and a stabilizer are wet-mixed together in water to form a slurry. Next, the slurry is dried and granulated. The resulting granules are then calcined to form primary powders.

Then, a color agent(s) is(are) added to each powder. An amount of addition of the color agent is appropriately adjusted such that color of each layer is developed. And with regard to each powder, zirconia is mixed and pulverized in water to a desired particle size to form a zirconia slurry. Next, the slurry is dried and granulated. In a case of addition of an additive such as aluminum oxide, titanium oxide, a binder etc., such may be added at the time of preparation of the primary powders or at the time of preparation of the secondary powders.

Next, press forming is carried out to produce a shaped product as a composition according to the present invention.

In a case where a pre-sintered body is not produced, a composition is fired at 1400° C. to 1600° C. and preferably at 1450° C. to 1550° C. to sinter the zirconia powders to produce a zirconia sintered body according to the present invention. Shaping to a desired shape may be performed in a stage of preparing the shaped product.

In a case where a pre-sintered body is produced, a composition is fired at 800° C. to 1200° C. to form a pre-sintered body. The pre-sintered body is then fired at 1400° C. to 1600° C., preferably 1450° C. to 1550° C. to sinter zirconia powders, thereby producing a zirconia sintered body according to the present invention. Shaping may be performed by cutting, machining etc in a stage of the pre-sintered body or after the sintering. Shaping may be performed with a CAD/CAM system.

A method of producing a dental product is the same as the above described production method except that a pre-sintered or a sintered body is shaped to the form of a crown.

According to the first embodiment, discoloration of a zirconia sintered body can be suppressed even if it is baked with a porcelain containing an antimony compound and/or a cerium compound. This makes it possible to facilitate production of a dental product having the same color as that of a patient's tooth.

The following embodiments will explain a sintered body, a pre-sintered body and a composition according to the present invention by focusing on their chromaticity and constitutions (compositions). The other items thereof are the same as those of the first embodiment.

A zirconia sintered body according to the second embodiment of the present invention will be explained.

A zirconia sintered body, a pre-sintered body and a composition according to the second embodiment may contain at least one of the coloring agent A and the coloring agent B, as well as the coloring agent C. A zirconia sintered body, a pre-sintered body and a composition may contain the coloring agent A of 0 mass % to 0.4 mass %, the coloring agent B of 0.0002 mass % to 0.03 mass % and the coloring agent C of 0.005 mass % to 0.1 mass %. This makes it possible to reproduce a specific color of a natural tooth.

Preferably, the zirconia sintered body according to the second embodiment has L* of 66 to 76, a* of −6 to 3 and b* of 3 to 27 in the L*a*b* color system.

The second embodiment can produce the same effect as that of the first embodiment.

A zirconia sintered body according to the third embodiment of the present invention will be explained.

A zirconia sintered body, a pre-sintered body and a composition according to the third embodiment may contain the coloring agent A of 0.002 mass % to 0.4 mass %, the coloring agent B of 0.0002 mass % to 0.03 mass % and the coloring agent C of 0.005 mass % to 0.1 mass %. This makes it possible to reproduce a specific color of a natural tooth.

Preferably, the zirconia sintered body according to the third embodiment has L* of 66 to 76, a* of −4 to 3 and b* of 3 to 27 in the L*a*b* color system.

The third embodiment can produce the same effect as that of the first embodiment.

A zirconia sintered body according to the fourth embodiment of the present invention will be explained.

A zirconia sintered body, a pre-sintered body and a composition according to the fourth embodiment may contain the coloring agent B of 0.01 mass % to 0.02 mass % and the coloring agent C of 0.06 mass % to 0.08 mass %. This makes it possible to reproduce the color of a specific natural tooth.

Preferably, the zirconia sintered body according to the fourth embodiment has L* of 70 to 74, a* of −6 to −3 and b* of 22 to 26 in the L*a*b* color system.

The fourth embodiment can produce the same effect as that of the first embodiment.

A zirconia sintered body according to the fifth embodiment of the present invention will be explained.

A zirconia sintered body, a pre-sintered body and a composition according to the fifth embodiment may contain at least one coloring agent selected from the group including the coloring agent A, the coloring agent B, the coloring agent C, the coloring agent D and the coloring agent E. Preferably, a zirconia sintered body, a pre-sintered body and a composition contain at least one of the coloring agent A, the coloring agent B and the coloring agent C, and at least one of the coloring agent D and the coloring agent E.

Preferably, the zirconia sintered body according to the fifth embodiment has L* of 64 to 75, a* of −3 to 3 and b* of 7 to 19 in the L*a*b* color system.

The fifth embodiment can produce the same effect as that of the first embodiment.

A zirconia sintered body according to the sixth embodiment of the present invention will be explained.

A zirconia sintered body, a pre-sintered body and a composition according to the sixth embodiment may contain the coloring agent C of 0.005 mass % to 0.02 mass % and the coloring agent E of 0.06 mass % to 0.08 mass %.

Preferably, the zirconia sintered body according to the sixth embodiment has L* of 74 to 75, a* of −2 to −1 and b* of 10 to 11 in the L*a*b* color system.

The sixth embodiment can produce the same effect as that of the first embodiment.

A zirconia sintered body according to the seventh embodiment of the present invention will be explained.

A zirconia sintered body, a pre-sintered body and a composition according to the seventh embodiment may contain the coloring agent C of 0.07 mass % to 0.09 mass % and the coloring agent D of 0.05 mass % to 0.2 mass %.

Preferably, the zirconia sintered body according to the seventh embodiment has L* of 68 to 69, a* of −3 to −2 and b* of 18 to 19 in the L*a*b* color system.

The seventh embodiment can produce the same effect as that of the first embodiment.

A zirconia sintered body according to the eighth embodiment of the present invention will be explained.

A zirconia sintered body, a pre-sintered body and a composition according to the eighth embodiment may contain the coloring agent B of 0.007 mass % to 0.06 mass % and the coloring agent D of 0.01 mass % to 0.06 mass %.

Preferably, the zirconia sintered body according to the eighth embodiment has L* of 64 to 71, a* of 0 to 2 and b* of 7 to 13 in the L*a*b* color system.

The eighth embodiment can produce the same effect as that of the first embodiment.

A zirconia sintered body according to the ninth embodiment of the present invention will be explained.

A zirconia sintered body, a pre-sintered body and a composition according to the ninth embodiment may contain the coloring agent A of 0.01 mass % to 0.04 mass %, the coloring agent C of 0.05 mass % to 0.07 mass % and the coloring agent D of 0.05 mass % to 0.08 mass %.

Preferably, the zirconia sintered body according to the ninth embodiment has L* of 67 to 69, a* of −2 to 0 and b* of 17 to 18 in the L*a*b* color system.

The ninth embodiment can produce the same effect as that of the first embodiment.

A zirconia sintered body according to the tenth embodiment of the present invention will be explained.

A zirconia sintered body, a pre-sintered body and a composition according to the tenth embodiment may contain the coloring agent A of 0.002 mass % to 0.3 mass %, the coloring agent B of 0.0005 mass % to 0.03 mass %, the coloring agent C of 0.005 mass % to 0.07 mass % and the coloring agent D of 0.004 mass % to 0.04 mass %.

Preferably, the zirconia sintered body according to the tenth embodiment has L* of 65 to 74, a* of −2 to 3 and b* of 9 to 18 in the L*a*b* color system.

The tenth embodiment can produce the same effect as that of the first embodiment.

A dental product according to the eleventh embodiment of the present invention will be explained.

A dental product contains a zirconia sintered body or a pre-sintered body according to the above embodiments. A dental product may further contain porcelain (for example, glass material) laminated on a zirconia sintered body. Porcelain may contain an anti-yellowing agent. As the anti-yellowing agent, an antimony compound, for example, may be used.

A dental product includes, for example, prosthesis such as a ceramic frame, a full-contour crown etc. A dental prosthesis is preferably of a tooth crown shape. Further, a dental product includes, for example, an orthodontic product (e.g. an orthodontic bracket) and a dental implant product (e.g. a dental implant abutment).

EXAMPLES

Zirconia sintered bodies added with the coloring agents shown in the following Tables were produced, and chromaticity of each of the resulting samples was measured. Initially, partially-stabilized zirconia powders containing 4 mol % of yttria as a stabilizer were mixed with the addition of the coloring agents. Next, the mixture of 1.2 g was put into a cylindrical metal mold (die) of about 18 mm in diameter and shaped under pressure of 30 kN to produce a shaped composition. Then, the shaped composition was fired at 1500° C. for 2 hours to produce a plate-like zirconia sintered body. Next, the sample surface was so polished that it was mirror finished (#2000 or more), to produce the sample(s). Then, a chromaticity measuring device (CE100-DC/US made by Olympus Corporation) and analysis software (Crystaleye) were used to measure chromaticity of each of the samples in the black background. Table 1 and Table 2 enumerate kinds and amounts of coloring agents added, and the results of the measurements of the chromaticity.

In Table 1 and Table 2, the coloring agent A is erbium oxide ($Er_2O_3$) made by Iwatani Sangyo Corporation. The coloring agent B is nickel oxide (NiO) made by Iwatsuki Kako Corporation. The coloring agent C is "Z-300 YELLOW" made by NITTO GANRYO KOGYO CO., LTD. which is a composite oxide of zirconium and vanadium ($(Zr, V)O_2$). The coloring agent D is "4555 GRAY" made by KAWAMURA-CHEMICAL CO., LTD. which is a mixture of a composite oxide of iron, cobalt and chromium ($(Co, Fe)(Fe, Cr)_2O_4$); a composite oxide of zirconium and silicon (zircon ($ZrSiO_4$)); silicon dioxide ($SiO_2$); and nickel oxide (NiO) (($(Co, Fe)(Fe, Cr)_2O_4/ZrSiO_4/SiO_2/NiO$). The coloring agent E is "H-150 GRAY" made by NITTO GANRYO KOGYO CO., LTD. which is a composite oxide of zirconium, silicon, cobalt and nickel (($(Co, Ni)O \cdot ZrSiO_4$)

Further, samples using praseodymium oxide as Comparative Examples were subjected to the same measurements as in Examples. In Comparative Examples 1 to 9, the coloring agent A is erbium oxide ($Er_2O_3$). The coloring agent F is iron oxide ($Fe_2O_3$). The coloring agent G is praseodymium oxide ($Pr_6O_{11}$).

All the samples of Examples 1 to 55 had color like a natural tooth. Further, Examples 1 to 55 had the same color as that of Comparative Examples 1 to 9. This revealed that the same color as a natural tooth's was able to be developed although praseodymium oxide and an iron compound were not used as a coloring agent.

Visual comparison of the color of the samples revealed that the samples of Examples 1 to 11 had a same system color(s). The samples of Examples 12 to 25 had a same system color(s). The samples of Examples 26 to 27 had a same system color(s). The samples of Examples 28 to 49 had a same system color(s). The samples of Examples 50 to 55 had a same system color(s). Accordingly, the samples of Examples 1 to 55 were able to be mainly classified into five groups. However, the samples of Examples 1 to 55 can be classified in a more detailed manner according to their color.

TABLE 1

| | Coloring Agent (wt %) | | | Chromaticity | | |
|---|---|---|---|---|---|---|
| | A | B | C | L* | a* | b* |
| Example 1 | 0.200 | 0.02 | 0.080 | 66.8 | 0.9 | 24.5 |
| Example 2 | 0.300 | 0.03 | 0.080 | 66.9 | 1.3 | 25.1 |
| Example 3 | 0.400 | 0.03 | 0.080 | 66.7 | 2.7 | 23.4 |
| Example 4 | 0.400 | 0.03 | 0.100 | 66.2 | 1.0 | 25.6 |
| Example 5 | 0.300 | 0.03 | 0.100 | 66.2 | 1.6 | 26.4 |
| Example 6 | 0.400 | 0.03 | 0.100 | 66.5 | 2.3 | 24.8 |
| Example 7 | 0.300 | 0.03 | 0.080 | 66.2 | 1.2 | 23.9 |
| Example 8 | 0.270 | 0.027 | 0.072 | 66.4 | 1.3 | 23.9 |
| Example 9 | 0.240 | 0.024 | 0.064 | 67.4 | 0.9 | 23.4 |
| Example 10 | 0.225 | 0.023 | 0.060 | 67.9 | 0.3 | 22.3 |
| Example 11 | 0.210 | 0.021 | 0.056 | 68.3 | 0.2 | 21.9 |
| Example 12 | 0 | 0.02 | 0.08 | 70.7 | −3.3 | 24.3 |
| Example 13 | 0 | 0.02 | 0.07 | 70.3 | −3.3 | 23.8 |
| Example 14 | 0 | 0.02 | 0.06 | 71.0 | −3.2 | 23.5 |
| Example 15 | 0 | 0.01 | 0.08 | 72.9 | −5.6 | 24.9 |
| Example 16 | 0 | 0.01 | 0.07 | 73.3 | −5.8 | 24.1 |
| Example 17 | 0 | 0.01 | 0.06 | 73.8 | −5.7 | 22.6 |
| Example 18 | 0 | 0.015 | 0.08 | 71.7 | −4.4 | 25.8 |
| Example 19 | 0 | 0.01 | 0.06 | 72.4 | −5.0 | 23.5 |
| Example 20 | 0.2 | 0.01 | 0.08 | 72.3 | −2.9 | 25.3 |
| Example 21 | 0.2 | 0.015 | 0.08 | 71.3 | −2.0 | 25.7 |
| Example 22 | 0.1 | 0.01 | 0.06 | 71.9 | −3.1 | 22.9 |
| Example 23 | 0.15 | 0.01 | 0.06 | 71.8 | −2.8 | 23.5 |
| Example 24 | 0.15 | 0.01 | 0.04 | 72.8 | −2.0 | 19.0 |
| Example 25 | 0.25 | 0.01 | 0.04 | 72.4 | −0.3 | 18.5 |
| Example 26 | 0.0048 | 0.0005 | 0.0128 | 75.5 | −1.8 | 5.4 |
| Example 27 | 0.0024 | 0.0002 | 0.0064 | 75.9 | −2.0 | 3.9 |

TABLE 2

| | Coloring Agent (wt %) | | | | | Chromaticity | | |
|---|---|---|---|---|---|---|---|---|
| | A | B | C | D | E | L* | a* | b* |
| Example 28 | 0 | 0 | 0.010 | 0 | 0.07 | 74.7 | −1.9 | 10.4 |
| Example 29 | 0 | 0 | 0.080 | 0.1 | 0 | 68.8 | −2.3 | 18.6 |
| Example 30 | 0.300 | 0 | 0.060 | 0.06 | 0 | 68.1 | 0.0 | 17.8 |
| Example 31 | 0.200 | 0 | 0.060 | 0.07 | 0 | 67.9 | −1.1 | 17.8 |
| Example 32 | 0 | 0.05 | 0 | 0.05 | 0 | 64.5 | 1.1 | 9.4 |
| Example 33 | 0 | 0.015 | 0 | 0.025 | 0 | 69.5 | 0.3 | 7.7 |
| Example 34 | 0 | 0.0075 | 0 | 0.0125 | 0 | 70.5 | 0.6 | 12.2 |
| Example 35 | 0.224 | 0.014 | 0.062 | 0.028 | 0 | 67.8 | 1.8 | 17.9 |
| Example 36 | 0.11 | 0.006 | 0.031 | 0.0175 | 0 | 71.4 | −0.6 | 16.2 |
| Example 37 | 0.088 | 0.0048 | 0.0248 | 0.014 | 0 | 72.5 | −0.8 | 12.4 |
| Example 38 | 0.066 | 0.0036 | 0.0186 | 0.0105 | 0 | 73.1 | −1.4 | 12.2 |
| Example 39 | 0.12 | 0.027 | 0.032 | 0.025 | 0 | 65.9 | 2.9 | 15.1 |
| Example 40 | 0.075 | 0.014 | 0.02 | 0.015 | 0 | 69.7 | −0.6 | 14.3 |
| Example 41 | 0.0375 | 0.007 | 0.01 | 0.0075 | 0 | 73.2 | −1.6 | 11.0 |
| Example 42 | 0.0975 | 0.017 | 0.026 | 0 | 0 | 68.6 | 0.0 | 15.9 |
| Example 43 | 0.04875 | 0.0085 | 0.013 | 0.00875 | 0 | 72.2 | −1.4 | 12.0 |
| Example 44 | 0.0525 | 0.023 | 0.014 | 0.0325 | 0 | 66.9 | 0.6 | 12.9 |
| Example 45 | 0.02625 | 0.0115 | 0.007 | 0.01625 | 0 | 71.3 | −0.8 | 10.1 |
| Example 46 | 0.0045 | 0.0018 | 0.012 | 0.025 | 0 | 68.7 | −0.1 | 12.6 |
| Example 47 | 0.00225 | 0.0009 | 0.006 | 0.0125 | 0 | 72.4 | −1.1 | 9.9 |
| Example 48 | 0.105 | 0.016 | 0.028 | 0.005 | 0 | 69.6 | 0.6 | 15.1 |
| Example 49 | 0.09 | 0.018 | 0.024 | 0.02 | 0 | 68.7 | 0.8 | 14.3 |
| Example 50 | 0.0518 | 0.0101 | 0.0138 | 0.01 | 0 | 71.9 | −0.5 | 11.7 |
| Example 51 | 0.0576 | 0.0127 | 0.0154 | 0.0135 | 0 | 71.1 | −0.4 | 12.6 |
| Example 52 | 0.054 | 0.0108 | 0.0144 | 0.012 | 0 | 71.4 | −0.6 | 12.2 |

TABLE 2-continued

| | Coloring Agent (wt %) | | | | | Chromaticity | | |
|---|---|---|---|---|---|---|---|---|
| | A | B | C | D | E | L* | a* | b* |
| Example 53 | 0.12 | 0.068 | 0.032 | 0.01 | 0 | 70.6 | 0.1 | 16.3 |
| Example 54 | 0.06 | 0.01 | 0.02 | 0.01 | 0 | 72.8 | −1.0 | 11.5 |
| Example 55 | 0.06 | 0.008 | 0.02 | 0.005 | 0 | 72.7 | −1.3 | 12.6 |

TABLE 3

| | Coloring Agent (wt %) | | | Chromaticity | | |
|---|---|---|---|---|---|---|
| | A | F | G | L* | a* | b* |
| Comparative Example 1 | 1.00 | 0.10 | 0.10 | 66.94 | 5.04 | 23.39 |
| Comparative Example 2 | 1.00 | 0.05 | 0.05 | 64.71 | 4.04 | 23.10 |
| Comparative Example 3 | 0.50 | 0.05 | 0.05 | 69.99 | 2.13 | 21.24 |
| Comparative Example 4 | 0.30 | 0.02 | 0.02 | 69.63 | 2.19 | 18.48 |
| Comparative Example 5 | 0.50 | 0.03 | 0.03 | 71.96 | 1.11 | 14.96 |
| Comparative Example 6 | 0.70 | 0.04 | 0.04 | 75.48 | −0.67 | 11.21 |
| Comparative Example 7 | 0.25 | 0.05 | 0.05 | 70.67 | 0.05 | 21.44 |
| Comparative Example 8 | 0.15 | 0.03 | 0.03 | 72.63 | −1.60 | 16.84 |
| Comparative Example 9 | 0.05 | 0.01 | 0.01 | 75.35 | −2.59 | 8.62 |

The samples of Example 9, Example 24, Example 32 and Comparative Example 2 were produced and baked with the porcelain, followed by the measurements of changes in color thereof. Table 4 to Table 7 shows the results of the measurements. Porcelain 1 shown in Table 4 to Table 7 is Cerabien ZR Translucent Tx made by Kuraray Noritake Dental Inc. Porcelain 2 is Cerabien ZR External Stain E Glaze made by Kuraray Noritake Dental Inc.

On one surface of the sample produced as with Examples 1 to 55, the porcelain was built up according to the manner of use of each porcelain. The thickness of Porcelain 1 was prepared (adjusted) using a (writing) brush to 0.2 mm+/−0.1 mm. The thickness of Porcelain 2 was prepared (adjusted) using a (writing) brush to 0.02 mm+/−0.01 mm. "Before Firing" shown in Table 4 to Table 7 means the sample on which the porcelain was not yet built up. "One-Time Firing" means the sample on which the porcelain was built up and fired. "Two-Time Firing" to "5-Time Firing" means the sample on which the porcelain was built up and fired 2 to 5 times respectively. For example, "2-Time Firing" means the sample obtained by firing the sample of "1-Time Firing" again. In the case where Porcelain 1 was built up, the sample was fired at 930° C. In the case where Porcelain 2 was built up, the sample was fired at 850° C. Chromaticity was so measured that the porcelain surface was directed to the measuring device. Color Difference ΔE is a difference in chromaticity between the pre-firing sample and the sample baked with the porcelain, which is calculated based on Formula 1. Color Difference ΔE can be calculated assuming, for example, that the chromaticity of the pre-firing sample is $(L^*_1, a^*_1, b^*_1)$ and chromaticity of the sample of 1-Time Firing is $(L^*_2, a^*_2, b^*_2)$. Color difference represents a degree of a change in color before and after porcelain being baked.

$$\Delta E = \sqrt{(L_1^* - L_2^*)^2 + (a_1^* - a_2^*)^2 + (b_1^* - b_2^*)^2} \qquad \text{FORMULA 1}$$

As to Porcelain 1, the color difference was smaller than 2.5 in Examples 9, 24 and 32 and 8.5 or more in Comparative Example 2. As to Porcelain 2, the color difference was smaller than 3 in Examples 9, 24 and 32 and 5.5 or more in Comparative Example 2. Hence, for both porcelains, the present invention was able to suppress discoloration caused by the anti-yellowing agents in the porcelains. Therefore, the present invention makes it possible to suppress discoloration and produce a zirconia sintered body and a dental product which have color like a natural tooth.

TABLE 4

| Measured Sample | Porcelain | Times of firing | Chromaticity | | | Color Difference |
|---|---|---|---|---|---|---|
| | | | L* | a* | b* | ΔE |
| Example 9 | Porcelain 1 | Before Firing | 67.5 | 0.7 | 23.0 | — |
| | | 1-Time Firing | 68.2 | 0.7 | 22.6 | 0.84 |
| | | 2-Time Firing | 68.4 | 0.8 | 21.7 | 1.62 |
| | | 3-Time Firing | 69.1 | 0.9 | 21.8 | 2.04 |
| | | 4-Time Firing | 69.1 | 0.9 | 21.9 | 1.97 |
| | | 5-Time Firing | 69.1 | 0.6 | 22.0 | 1.88 |
| | Porcelain 2 | Before Firing | 67.5 | 0.8 | 23.3 | 2.42 |
| | | 1-Time Firing | 69.6 | 0.4 | 22.2 | 2.48 |
| | | 2-Time Firing | 69.4 | 0.5 | 21.8 | 2.47 |
| | | 3-Time Firing | 69.3 | 0.4 | 21.7 | 2.42 |

TABLE 5

| Measured Sample | Porcelain | Times of Firing | Chromaticity | | | Color Difference |
|---|---|---|---|---|---|---|
| | | | L* | a* | b* | ΔE |
| Example 24 | Porcelain 1 | Before Firing | 72.5 | −2.2 | 19.4 | — |
| | | 1-Time Firing | 73.2 | −2.2 | 18.4 | 1.22 |
| | | 2-Time Firing | 73.1 | −2.0 | 17.7 | 1.82 |
| | | 3-Time Firing | 74.0 | −2.2 | 17.8 | 2.17 |
| | | 4-Time Firing | 73.9 | −2.2 | 18.0 | 1.93 |
| | | 5-Time Firing | 73.9 | −2.2 | 18.1 | 1.92 |
| | Porcelain 2 | Before Firing | 72.3 | −2.4 | 18.9 | 2.23 |
| | | 1-Time Firing | 74.3 | −2.6 | 17.9 | 2.10 |

TABLE 5-continued

| Measured Sample | Times of Porcelain Firing | Chromaticity L* | a* | b* | Color Difference $\Delta E$ |
|---|---|---|---|---|---|
| | 2-Time Firing | 74.2 | −2.5 | 17.9 | 2.03 |
| | 3-Time Firing | 74.0 | −2.5 | 17.7 | 2.23 |

TABLE 6

| Measured Sample | Porcelain | Times of Firing | Chromaticity L* | a* | b* | Color Difference $\Delta E$ |
|---|---|---|---|---|---|---|
| Example 32 | Porcelain 1 | Before Firing | 64.4 | 2.1 | 10.8 | — |
| | | 1-Time Firing | 66.2 | 1.8 | 11.1 | 1.84 |
| | | 2-Time Firing | 65.6 | 2.1 | 11.7 | 1.49 |
| | | 3-Time Firing | 66.2 | 1.9 | 11.7 | 1.95 |
| | | 4-Time Firing | 66.0 | 2.0 | 11.8 | 1.91 |
| | | 5-Time Firing | 66.1 | 1.9 | 11.7 | 1.89 |
| | Porcelain 2 | Before Firing | 64.2 | 2.1 | 11.1 | — |
| | | 1-Time Firing | 66.0 | 1.9 | 10.4 | 1.89 |
| | | 2-Time Firing | 66.1 | 1.8 | 10.5 | 2.03 |
| | | 3-Time Firing | 66.1 | 1.9 | 10.3 | 2.09 |

TABLE 7

| Measured Sample | Porcelain | Times of Firing | Chromaticity L* | a* | b* | Color Difference $\Delta E$ |
|---|---|---|---|---|---|---|
| Comparative Example 2 | Porcelain 1 | Before Firing | 68.5 | 3.8 | 21.1 | — |
| | | 1-Time Firing | 71.1 | 4.1 | 12.8 | 8.64 |
| | | 2-Time Firing | 71.8 | 4.1 | 11.8 | 9.89 |
| | | 3-Time Firing | 71.9 | 4.1 | 11.7 | 9.92 |
| | Porcelain 2 | Before Firing | 69.2 | 2.7 | 19.4 | — |
| | | 1-Time Firing | 71.8 | 3.2 | 14.6 | 5.55 |

For reference, the following Tables show the results of element analysis of the coloring agent C, the coloring agent D and the coloring agent E which were used in Examples. Table 8 shows the results of analysis of the coloring agent C, Table 9 shows the results of analysis of the coloring agent D, and Table 10 shows the results of analysis of the coloring agent E. The following Tables show the ratios of mass of the elements in terms of their oxides, which however does not necessarily mean that the coloring agents contain their elements in the form of their oxide shown in the Tables therein.

TABLE 8

| Coloring Agent C | |
|---|---|
| $ZrO_2$ | 83.21 wt % |
| $Fe_2O_3$ | 0.9568 wt % |
| NiO | 0.0140 wt % |
| $V_2O_5$ | 5.365 wt % |
| $Nb_2O_5$ | 0.0659 wt % |
| $TiO_2$ | 4.625 wt % |
| $SiO_2$ | 3.168 wt % |
| Others | 2.594 wt % |

TABLE 9

| Coloring Agent D | |
|---|---|
| $ZrO_2$ | 49.02 wt % |
| $Fe_2O_3$ | 5.944 wt % |
| $Cr_2O_3$ | 2.649 wt % |
| MnO | 1.681 wt % |
| NiO | 1.093 wt % |
| $Co_2O_3$ | 3.740 wt % |
| $V_2O_5$ | 0.0525 wt % |
| $SiO_2$ | 33.07 wt % |
| Others | 2.751 wt % |

TABLE 10

| Coloring Agent E | |
|---|---|
| $ZrO_2$ | 58.97 wt % |
| $Fe_2O_3$ | 0.1338 wt % |
| NiO | 9.818 wt % |
| $Co_2O_3$ | 2.866 wt % |
| $SiO_2$ | 24.34 wt % |
| Others | 3.870 wt % |

The disclosure of each of the above-identified patent literatures is incorporated herein by reference thereto. Although the zirconia composition, the zirconia pre-sintered body and the zirconia sintered body, and the dental product according to the prevent invention are explained based on the above Embodiments, the present invention is not limited to the above Embodiments, and may include any modification, change and improvement to the disclosed various elements (including, for example, each element in the Claims, each element in the Embodiments and Examples and each element in the Drawings) based on the basic technical idea of the present invention within the entire disclosure of the present invention. Further, within the entire disclosure of the present invention, various combinations, replacements (substitutions) and selections (including exclusion and deletion) of the various disclosed elements (including, for example, each element in the Claims, each element in the Embodiments and Examples and each element in the Drawings) are available.

A further problem(s), object(s) and developed mode(s) of the present invention may be made clear from the entire disclosure, including the Claims, of the present invention.

With regard to a numerical range(s) in the Description, it should be interpreted that any value(s) and sub-range(s) that are included in the range(s) are concretely disclosed even if not specially mentioned.

The invention claimed is:
1. A zirconia sintered body, comprising:
at least two coloring agents selected from the group consisting of
a coloring agent A: erbium oxide,
a coloring agent B: nickel oxide, a coloring agent C: a composite oxide of zirconium and vanadium,
a coloring agent D: a mixture of a composite oxide of iron, cobalt and chromium, a composite oxide of zirconium and silicon, silicon dioxide and nickel oxide, and
a coloring agent E: a composite oxide of zirconium, silicon, cobalt and nickel.

2. The zirconia sintered body according to claim 1, comprising:
at least one of the coloring agent A, the coloring agent B and the coloring agent C; and
at least one of the coloring agent D and the coloring agent E.

3. The zirconia sintered body according to claim 1, comprising:
the coloring agents C and E,
wherein
the coloring agent C is contained in an amount of 0.005 to 0.02 mass %; and
the coloring agent E is contained in an amount of 0.06 to 0.08 mass %.

4. The zirconia sintered body according to claim 1, comprising:
the coloring agents C and D,
wherein
the coloring agent C is contained in an amount of 0.07 to 0.09 mass %; and
the coloring agent D is contained in an amount of 0.05 to 0.2 mass %.

5. The zirconia sintered body according to claim 1, comprising:
the coloring agents B and D,
wherein
the coloring agent B is contained in an amount of 0.007 to 0.06 mass %; and
the coloring agent D is contained in an amount of 0.01 to 0.06 mass %.

6. The zirconia sintered body according to claim 1, comprising:
the coloring agents A, C and D,
wherein
the coloring agent A is contained in an amount of 0.01 to 0.04 mass %;
the coloring agent C is contained in an amount of 0.05 to 0.07 mass %; and
the coloring agent D is contained in an amount of 0.05 to 0.08 mass %.

7. The zirconia sintered body according to claim 1, comprising:
the coloring agents A, B, C and D,
wherein
the coloring agent A is contained in an amount of 0.002 to 0.3 mass %;
the coloring agent B is contained in an amount of 0.0005 to 0.03 mass %;
the coloring agent C is contained in an amount of 0.005 to 0.07 mass %; and
the coloring agent D is contained in an amount of 0.004 to 0.04 mass %.

8. A composition, comprising:
zirconium oxide,
yttrium oxide, and
a coloring agent,
wherein the coloring agent comprises at least two coloring agents selected from the group consisting of
a coloring agent A: erbium oxide,
a coloring agent B: nickel oxide,
a coloring agent C: a composite oxide of zirconium and vanadium,
a coloring agent D: a mixture of a composite oxide of iron, cobalt and chromium, a composite oxide of zirconium and silicon, silicon dioxide and nickel oxide,
and
a coloring agent E: a composite oxide of zirconium, silicon, cobalt and nickel.

9. The composition according to claim 8, comprising:
at least one of the coloring agent A, the coloring agent B and the coloring agent C; and
at least one of the coloring agent D and the coloring agent E.

10. The composition according to claim 8, comprising:
the coloring agents C and E,
wherein
the coloring agent C is contained in an amount of 0.02 to 0.03 mass %; and
the coloring agent E is contained in an amount of 0.06 to 0.08 mass %.

11. The composition according to claim 8, comprising:
the coloring agents C and D,
wherein
the coloring agent C is contained in an amount of 0.07 to 0.09 mass %; and
the coloring agent D is contained in an amount of 0.08 to 0.12 mass %.

12. The composition according to claim 8, comprising:
the coloring agents B and D,
wherein
the coloring agent B is contained in an amount of 0.007 to 0.06 mass; and
the coloring agent D is contained in an amount of 0.01 to 0.06 mass %.

13. The composition according to claim 8, comprising:
the coloring agents A, C and D,
wherein
the coloring agent A is contained in an amount of 0.01 to 0.04 mass %;
the coloring agent C is contained in an amount of 0.05 to 0.07 mass %; and
the coloring agent D is contained in an amount of 0.05 to 0.08 mass %.

14. The composition according to claim 8, comprising:
the coloring agents A, B, C and D,
wherein
the coloring agent A is contained in an amount of 0.002 to 0.3 mass %;
the coloring agent B is contained in an amount of 0.0005 to 0.03 mass %;
the coloring agent C is contained in an amount of 0.005 to 0.07 mass %; and
the coloring agent D is contained in an amount of 0.004 to 0.04 mass %.

15. A pre-sintered body, produced by firing a composition according to claim 8 at 800° C. to 1200° C.

16. A zirconia sintered body, produced by firing a composition according to claim 8 at 1300° C. to 1600° C.

17. A pre-sintered body, comprising:
zirconium oxide,
yttrium oxide, and
a coloring agent,
wherein the coloring agent comprises at least two coloring agents selected from the group consisting of a coloring agent A: erbium oxide,
a coloring agent B: nickel oxide,
a coloring agent C: a composite oxide of zirconium and vanadium,
a coloring agent D: a mixture of a composite oxide of iron, cobalt and chromium, a composite oxide of zirconium and silicon, silicon dioxide and nickel oxide,
and
a coloring agent E: a composite oxide of zirconium, silicon, cobalt and nickel.

18. The pre-sintered body according to claim 17, comprising:
at least one of the coloring agent A, the coloring agent B and the coloring agent C; and
at least one of the coloring agent D and the coloring agent E.

19. The pre-sintered body according to claim 17, comprising:
the coloring agents C and E,
wherein
the coloring agent C is contained in an amount of 0.02 to 0.03 mass %; and
the coloring agent E is contained in an amount of 0.06 to 0.08 mass %.

20. The pre-sintered body according to claim 17, comprising:
the coloring agents C and D,
wherein
the coloring agent C is contained in an amount of 0.07 to 0.09 mass %; and
the coloring agent D is contained in an amount of 0.08 to 0.12 mass %.

21. The pre-sintered body according to claim 17, comprising:
the coloring agents B and D,
wherein
the coloring agent B is contained in an amount of 0.007 to 0.06 mass %; and
the coloring agent D is contained in an amount of 0.01 to 0.06 mass %.

22. The pre-sintered body according to claim 17, comprising:
the coloring agents A, C and D,
wherein
the coloring agent A is contained in an amount of 0.01 to 0.04 mass %;
the coloring agent C is contained in an amount of 0.05 to 0.07 mass %; and
the coloring agent D is contained in an amount of 0.05 to 0.08 mass %.

23. The pre-sintered body according to claim 17, comprising:
the coloring agents A, B, C and D,
wherein
the coloring agent A is contained in an amount of 0.002 to 0.3 mass %;
the coloring agent B is contained in an amount of 0.0005 to 0.03 mass %;
the coloring agent C is contained in an amount of 0.005 to 0.07 mass %; and
the coloring agent D is contained in an amount of 0.004 to 0.04 mass %.

24. A zirconia sintered body, produced by firing a pre-sintered body according to claim 17 at 1300° C. to 1600° C.

25. A dental product, comprising a zirconia sintered body according to claim 1.

26. The dental product according to claim 25, further comprising a porcelain layer laminated on the zirconia sintered body,
wherein the porcelain layer comprises an anti-yellowing material.

27. The dental product according to claim 26, wherein the anti-yellowing material comprises at least one of an antimony compound and a cerium compound.

* * * * *